United States Patent [19]

Voronkov et al.

[11] 4,283,419
[45] Aug. 11, 1981

[54] PREPARATION FOR RAISING THE FERTILITY OF ANIMALS

[76] Inventors: Mikhail G. Voronkov, ulitsa Lermontova, 315, kv. 32; Ada T. Platonova, ulitsa Lermontova, 313, kv. 31; Nikolai L. Simbirtsev, ulitsa Chaikovskogo, 20, kv. 2; Valery M. Dyakov, ulitsa Lermontova, 263, kv. 23, all of Irkutsk; Andrei P. Dyban, prospekt Engelsa, 28, kv. 130, Leningrad; Igor G. Kuznetsov, ulitsa Lermontova, 273, kv. 86, Irkutsk, all of U.S.S.R.

[21] Appl. No.: 956,733

[22] Filed: Nov. 1, 1978

[51] Int. Cl.³ ............................................. A61K 31/205
[52] U.S. Cl. ..................................................... 424/316
[58] Field of Search ......................................... 424/316

[56] References Cited

FOREIGN PATENT DOCUMENTS 2432393  1/1975  Fed. Rep. of Germany ........... 424/316

Primary Examiner—Frederick E. Waddell
Attorney, Agent, or Firm—J. Harold Nissen

[57] ABSTRACT

A preparation for raising fertility in animals, comprising tris-(2-ethoxy)-ammonium-orthocresoxyacetate with the following formula:

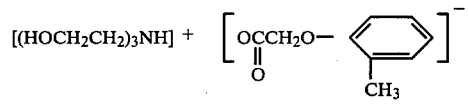

Said substance is added to the feed of animals in 2 to 50 mg/kg doses. The preparation prevents embryonal death of fetuses, increases natality and also raises the weight and viability of the fetus.

2 Claims, No Drawings

PREPARATION FOR RAISING THE FERTILITY OF ANIMALS

This invention relates to animal breeding, and more particularly to preparations for raising the fertility of animals.

A steep drop of natality in various farm animals is taking place at present in the animal breeding industry of many countries, which results in a reduction of food stocks and also raw materials (wool, hides) for industry. This prompted a search for preparations to induce higher animal natality.

BACKGROUND OF THE INVENTION

Among the means for raising the natality of animals and the viability of their fetuses, the following hormonal preparations are known to be most effective: pregnant mare serum (PMS), super-mutagen (1–4 bis-diazocetyl butane), progesterone, prostaglandins and vitamins.

The use of PMS in sows raises fertility by 1 to 2 piglets, but reduces weight and raises peritoneal mortality of piglets by more than 12%.

The use of super-mutagen for stimulating fertility in mink raises natality up to 7 cubs, as against 6 in the controls.

Progesterone and other hormonal preparations raise the conception rate in sheep by 90 to 96%. Yet, the high cost of hormonal preparations and the complexity of their manufacture reduce their worth very much, hindering their wide-scale introduction into animal breeding practice. In this connection, the US Animal Breeding Association has no plans for introducing hormonal preparations and prostaglandins to raise estrus synchronization in animals.

Trials carried out in Great Britain to check-up sheep fertility assessment methods showed hormonal stimulation to increase the fall of lambs, but this is accompanied by a reduction of their weight, while peritoneal mortality reaches 80 to 85%.

OBJECT OF THE INVENTION

It is an object of the invention to provide a new preparation for raising the fertility of animals.

SUMMARY OF THE INVENTION

This object is achieved by that a preparation is provided, intended for raising the fertility of animals, the active principle of which, according to the invention, is tris-(2-ethoxy)-ammonium-orthocresoxyacetate with the following formula:

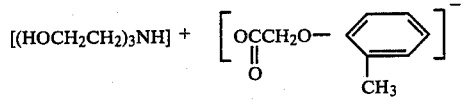

This substance may be used separately or in combination with a carrier. It is administered with the feed in 2 to 50 mg/kg doses.

The proposed preparation does not worsen the quality of the meat and milk, nor does it produce any untoward side effects; it effectively raises the natality of animals and the viability of their fetuses.

The substance possesses no embryotoxic or embryotropic effect. It stimulates the maturation of primordial follicles of the spermatogenic epithelium of the gonads, increases the motility of the spermatozoa, synchronizes estrus in the animals, prevents embryonal deaths, raises the weight of fetuses and their viability (survival).

DETAILED DESCRIPTION OF THE INVENTION

The toxicity of tris-(2-ethoxy)-ammonoim-orthocresoxyacetate was studied in mice, rats and rabbits by oral introduction into the stomach. The study showed that the substance has low toxicity: the maximum tolerance dose is 2,600 mg/kg, the $LD_{50}$ is 3,570 mg/kg, and the $LD_{100}$ is 3,800 mg/kg. Multiple administration of the substance (for 10 days and more) in 50 and 100 mg/kg doses increases the weight of the animals, increases the size of their lymphoid organs, and increases the number of their embryos.

The substance given in 50 and 100 mg/kg doses does not harmfully affect the cardiovascular, peripheral and central nervous systems, respiration, blood pressure, the excretory function of the kidneys, while somewhat increasing the protective reaction of the liver. Said doses have a somewhat stimulating effect on medullary hemopoiesis, which promotes the formation of antibody-producing plasma cells. This, in turn, activates the protective forces of the animal organism.

A study of said substance for ovogenesis and spermatogenesis was carried out in sexually mature mice and rats. The animals were administered 25, 50 and 100 mg/kg doses of the substance orally into the stomach for 10 days.

After ten days of administration of the compound part of the mice and rats were slaughtered. The effect of the substance on the animals' ovogenesis and spermatogenesis was judged by histological sections of the ovaries and gonads.

50 and 100 mg/kg doses of the substance stimulated the maturation of the primordial follicles and the ovaries, as well as of the spermatogenic epithelium of the testes. The remaining animals given the substance (males and females) were mated in order to study possible delayed contraceptive effect and its influence on the fertility of the progeny in subsequent generations.

50 and 100 mg/kg doses of the substance render no remote contraceptive effect, nor do they cause abortions or fetal deformities either in subsequent pregnancies or upon reaching sexual maturity in the offspring born of the test animals in the second or third generations. In each case, the offspring born was absolutely normal; nor were they any cases of cancerogenesis. The introduction of the substance into the semen diluent of bulls and rams in a concentration of 2 to 5 mg/l raises the motility of spermatozoa for 72 to 100 hours.

The substance was studied for embryonal death in sexually mature rats weighing 200 to 250 g. Female rats were given intragastrally 10%, 20% and 40% acqueous solutions of the substance, i.e., 50, 100 and 200 mg/kg doses for ten days every day. The animals were slaughtered at the end of this ten day period of administration. The resorption of the fetuses was assessed by the number of corpora luteum and embryos. There were ten animals in each group, and the tests were repeated 2–3 times. The effect of said substance on the intrauterine development of the embryos is illustrated in Table 1.

TABLE 1

Embryo Development in Rats Given Said Substance Before Conception

Effect of Preparation on Rat Embryonal Resorption

| Number of rats | Doses mg/kg | Number of corpora luteum per rat | Average number of normal embryos | Average weight of embryo, mg | Number of perished embryos |
|---|---|---|---|---|---|
| 10 | — | 12 ± 2 | 7 ± 1.5 | 122 ± 8 | 5 |
| 10 | 50 | 11 ± 2 | 10 ± 1.6 | 142 ± 7.5 | 1 |
| 10 | 100 | 12 ± 3 | 10.8 ± 1.2 | 165 ± 1 | 2 |
| 10 | 200 | 12 ± 2.5 | 8.1 ± 3 | 154 ± 9 | 4 |

The Table shows that 50 and 100 mg/kg doses of the proposed substance sharply reduce the resorption of embryos, whereas the 200 mg/kg dose somewhat increase embryonal deaths, as compared to the 50 mg/kg dose. The administration of the preparation to rats for ten days following conception raises the weight and number of normally developing embryos. Part of the animals in the test and control groups were slaughtered eleven days after conception, while the remaining animals were left to give birth and suckle their litters.

Table 2 presents the results of tests to determine the influence of the substance on the intrauterine development of the embryos following conception.

TABLE 2

Effect of the Preparation on Intrauterine Development of Embryos Following Conception

| Total number of animals | Slaughtered animals | Dose of preparation, mg/kg | Average number of embryos | Average weight of embryos, mg | Average weight gain of embryos over controls, mg | Of these born: total | live | dead | post-natal mortality |
|---|---|---|---|---|---|---|---|---|---|
| 20 | 10 | 0 | 7 ± 3 | 121 ± 15 | — | 65 | 59 | 6 | 7 |
| 20 | 10 | 50 | 10 ± 2 | 142 ± 18 | 21 | 92 | 91 | 1 | — |
| 20 | 10 | 100 | 11 ± 3 | 185 ± 12 | 64 | 98 | 95 | 3 | 2 |
| 20 | 10 | 200 | 8.2 ± 2 | 157 ± 20 | 36 | 84 | 77 | 7 | 10 |

Table 2 shows that 50 and 100 mg/kg doses of the substance raised the number and weight of the embryos, and the same doses caused the maximum natality of the offspring and its viability.

Besides, the examinations showed that said substance also affects embryonal development at different terms of pregnancy in the rats.

Table 3 presents the results of studies into the effect of the preparation on the embryonal development in rats at different terms of pregnancy.

TABLE 3

Effect of the Preparation on Embryonal Development in Rats

| Dose of Substance mg/kg | Number of females | Time of administration | Number of corpora luteum | Total number of normal embryos | Average number of embryos per rat | Before implantation Absolute number | % | After implantation Absolute number | % |
|---|---|---|---|---|---|---|---|---|---|
| 0 control | 25 | — | 285 | 242 | 10 | 40 | 14 | 3 | 1.2 |
| 50 | 15 | One day before pregnancy | 186 | 174 | 11.6 | 9 | 5 | 3 | 1.7 |
| 100 | 10 | Four days before pregnancy | 113 | 102 | 10.2 | 7 | 6.2 | 4 | 3.7 |
| 400 | 5 | Ninth day of pregnancy | 60 | 62 | 10.4 | 7 | 11.7 | 1 | 1.9 |

The Table indicates that the proposed substance steeply reduces embryonic resorption.

The preparation was tested in farm animals, taking sows and sheep. The preparation was added to the feed of a group of breeding sows, taking 10 mg/kg doses. After fifteen days of administering the preparation, the sows were inseminated with the semen of a boar of known fertility. Thirty days after insemination, part of the sows were slaughtered for determining embryonal mortality, leaving the rest to farrow and suckle their litters. The results are presented in Table 4.

TABLE 4

Effect of the Preparation on Reproductive Activity (Natality or Fertility of Sows)

| Total number of animals | Dose mg/kg | Average number or corpora-luteum | Average number of embryos | Embryonic resorption % | Births total | live | Average weight of piglet, g | died within one month |
|---|---|---|---|---|---|---|---|---|
| 8, four of them slaughtered | 0 | 42.1 | 30.2 | 28 | 24 | 22 | 1,150 | 6 |
| 10, six of them | | | | | | | | |

TABLE 4-continued

Effect of the Preparation on Reproductive Activity (Natality or Fertility of Sows)

| Total number of animals | Dose mg/kg | Average number or corpora-luteum | Average number of embryos | Embryonic resorption % | Births total | Births live | Average weight of piglet, g | died within one month |
|---|---|---|---|---|---|---|---|---|
| sluaghtered | 10 | 45.2 | 38.3 | 15 | 60 | 57 | 1,300 | 8 |

These data show that the preparation increased piglet natality by more than 60%, weight by 13% and survival by 14%.

For testing the preparation in ewes, it was given in 2, 4 and 6 mg/kg doses. According to the conditions of the test, the preparation was added daily into their feed for 15 days prior to artificial insemination. Following insemination the preparation was given for another 10 days with the purpose of preventing embryonal mortality.

The test was conducted in three groups of Precoce ewes, fifty animals in each. The first group of ewes was given 2 mg/kg doses, the second, 4 mg/kg doses and the third, 6 mg/kg. Similar control groups of ewes did not receive the preparation. In each group, two animals were slaughtered. The theoretical natality of the ewes without the slaughtered ones was: 1st group—147 lambs per 100 ewes, 2nd group—166, 3rd group—150; in the controls, the natality was 83. The results are presented in Table 5.

high biological activity, low production cost, all point to the fact that it is a promising preparation for wide use in animal breeding practice and fur farming.

Tris-(2-ethoxy)-ammonium-orthocresoxyacetate is a substance known in the art; it appears as a white crystalline, odorless, bitterish powder, well soluble in water, stable in storage. Its melting point is 79° to 81° C.

Said substance is readily produced through the interaction of triethanol amine with ortho-cresoxy acetic acid heated in the medium of an organic solvent.

An example will now be described of obtaining tris-(2-ethoxy)-ammonium-orthocresoxyacetate.

A solution of 149.2 g (1.0 mole) of triethanolamine in 150 ml of ethanol is poured into a solution of 174.5 g (1.05 moles) of orthocresoxy acetic acid in 500 ml of ethanol. The reaction mixture is heated to the boiling point, then cooled down to a temperature of 20° C., and 100 ml of diethyl ether are added. The white crystalline precipitate that falls out is drawn off, washed with ether, and dried under vacuum. The yield of the prod-

TABLE 5

Results of Testing the Preparation for Reproductive Activity in Precoce Ewes

| No. of group | Type of group | Number of ewes in group | Daily dose, mg/kg | total | triples | % of triples | twins | % of twinning | number of twin lambs | % of twins | total lamb mortality | mortality rate % | average lamb birth rate per 100 ewes | lamb birth rate increase over controls, % |
|---|---|---|---|---|---|---|---|---|---|---|---|---|---|---|
| 1 | Control | 48 | 0 | 57 | — | — | 9 | 15.7 | 18 | 31.3 | 3 | 5.2 | 118.7 | — |
|   | Test | 48 | 2 | 72 | — | — | 24 | 33.3 | 48 | 66.6 | 1 | 1.3 | 150 | 27 |
| 2 | Control | 48 | 0 | 56 | — | — | 9 | 16 | 18 | 31.1 | 5 | 8.9 | 116.6 | — |
|   | Test | 48 | 4 | 74 | — | — | 26 | 35.1 | 52 | 70.2 | 2 | 2.5 | 154 | 30 |
| 3 | Control | 48 | 0 | 58 | — | — | 10 | 17.2 | 20 | 34.4 | 2 | 3.4 | 120 | — |
|   | Test | 48 | 6 | 71 | 1 | 1.4 | 23 | 32.3 | 46 | 67.7 | 1 | 1.4 | 147 | 22 |

As Table 5 makes clear, the number of lambs in all the test groups exceeds the controls considerably. Characteristically, the number of twin-pregnancies increased, and the lamb mortality rate is lower than in the controls. The test lamb birth rate was 20 to 30% higher than in the control groups.

The best results were obtained in the first and second groups, where the dose of the substance was 2 to 4 mg/kg. The preparation did not terminate pregnancies in the ewes, nor did it cause any abortions or deformity of the lambs. Subsequent observations showed that, feeding and other conditions being equal, lamb mortality in the test groups was three times lower than in the controls.

Thus, the results of investigations in test animals, both in the laboratory and on the farms, demonstrate that the proposed preparation considerably raises natality and increases the viability of normally developed fetuses, and new-born animals. The preparation's low toxicity, uct is 295 g (93.6% of theoretical); the melting point is 82° to 83° C.

What is claimed is:

1. A method for raising fertility in a farm animal comprising administering to the animal a preparation, the active principle of which is tris-(2-ethoxy)-ammonium-orthocresoxyacetate having the formula:

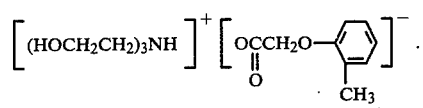

wherein the amount administered is between 2 and 50 mg/kg per dose.

2. The method of claim 1 wherein the amount administered is from 2 to 6 mg/kg per day.